United States Patent
Wang et al.

(10) Patent No.: US 8,563,307 B2
(45) Date of Patent: Oct. 22, 2013

(54) TREATMENT OF IMMUNOSUPPRESSION-RELATED DISORDERS

(76) Inventors: James Wang, Monterey Park, CA (US); Lufen Chang, Monterey Park, CA (US); Yun Yen, Arcadia, CA (US)

( * ) Notice: Subject to any disclaimer, the term of this patent is extended or adjusted under 35 U.S.C. 154(b) by 558 days.

(21) Appl. No.: 12/391,581

(22) Filed: Feb. 24, 2009

(65) Prior Publication Data
US 2010/0215622 A1     Aug. 26, 2010

(51) Int. Cl.
| | |
|---|---|
| *C12N 5/08* | (2006.01) |
| *C12N 5/00* | (2006.01) |
| *A01N 63/00* | (2006.01) |
| *A01N 65/00* | (2009.01) |

(52) U.S. Cl.
USPC .................. 435/372; 435/325; 424/93.7

(58) Field of Classification Search
USPC ................... 424/93.7; 435/325, 372
See application file for complete search history.

(56) References Cited

U.S. PATENT DOCUMENTS

| | | |
|---|---|---|
| 6,916,654 B1 | 7/2005 | Sims et al. |
| 6,986,887 B2 | 1/2006 | Lawman et al. |
| 2003/0161817 A1 | 8/2003 | Young et al. |
| 2006/0035373 A1 | 2/2006 | Zhang et al. |
| 2006/0171931 A1 | 8/2006 | Rudnicki et al. |
| 2006/0252150 A1 | 11/2006 | Cheng |
| 2008/0102521 A1 | 5/2008 | Sugaya et al. |
| 2008/0152665 A1 | 6/2008 | Leclerc et al. |
| 2008/0305079 A1 | 12/2008 | Chen |
| 2009/0104160 A1 | 4/2009 | Young et al. |

FOREIGN PATENT DOCUMENTS

| | | |
|---|---|---|
| EP | 1632563 | 3/2006 |
| WO | WO 2006/028723 A1 * | 3/2006 |
| WO | WO 2007/100845 | 9/2007 |

OTHER PUBLICATIONS

Hamman et al., 2005, Biodrugs, vol. 19, No. 3, p. 165-177.*
Torchilin et al., 2003, DDT, vol. 8, No. 6, p. 259-266.*
Li et al., 2009, Transplant Immunology, vol. 21, p. 70-74.*
Sprangers et al., 2008, Kidney International, vol. 74, p. 14-21.*
Arechaga et al.; "Characterisation of new intracellular membranes in *Escherichia coli* accompanying large scale over-production of the b subunit of $F_1F_0$ ATP synthase"; FEBS Letters 482:215-219 (2000).
Bizzetto et al.; "Outcomes after related and unrelated umbilical cord blood transplantation for hereditary bone marrow failure syndromes other than fanconi anemia"; Haematologica 96(1)134-141 (2011).
Dolcetti et al.; "Myeloid-derived suppressor cell role in tumor-related inflammation"; Cancer Letters, 267:216-225 (2008).
Serafini et al.; "Myeloid suppressor cells in cancer: recruitment, phenotype, properties, and mechanisms of immune suppression"; 16:53-65 (2006).
Sinha et al.; "Prostaglandin E2 promotes tumor progression by inducing myeloid-derived suppressor cells"; Cancer Res, 67(9):4507-4513 (2007).
Talmadge; "Pathways mediating the expansion and immunosuppressive activity of myeloid-derived suppressor cells and their relevance to cancer therapy"; Clin Cancer Res, 13(18):5243-5248 (2007).
Tu et al.; "Overexpression of interleukin-1beta induces gastric inflammation and cancer and mobilizes myeloid-derived suppressor cells in mice"; Cancer Cell, 14(5):408-419 (2008).
Young et al.: "Adult-derived stem cells and their potential for use in tissue repair and molecular medicine"; J. Cell. Mol. Med., 9(3):753-769 (2005).

* cited by examiner

*Primary Examiner* — Shin-Lin Chen

(57) ABSTRACT

Disclosed are methods of using blastomere-like stem cells to (1) decrease the level of myeloid-derived suppressor cells, (2) modulate immune response, (3) overcome a myeloid-derived suppressor cell-mediated immunosuppression, and (4) treat a cellular proliferative disorder. The blastomere-like stem cells, positive for CD66e, can be isolated from blood, bone marrow, or skeletal muscle.

9 Claims, No Drawings

TREATMENT OF IMMUNOSUPPRESSION-RELATED DISORDERS

BACKGROUND

The immune system defends an organism against pathogen infection, cellular transformation, and physical or chemical damage. When the immune system is less active than normal, immunodeficiency or immunosuppression occurs, resulting in life-threatening infections or cancer. Immunosuppression can either be the result of a disease, or be produced by pharmaceuticals or an infection. Systemic immunosuppression has been found to be associated with abnormal myelopoiesis secondary to tumor growth, myelosuppressive therapy, and growth factor administration and subsequent expansion/mobilization of bone marrow derived immunosuppressive cells. These myeloid-derived suppressor cells (MDSCs) reduce activated T-cell number and inhibit T-cell function by multiple mechanisms, thereby leading to immunosuppression and tolerance. Thus, MDSCs have a pro-tumor role. In addition, MDSCs have pleiotropic activities that include induction of mutations in the tumor microenvironment, promotion of angiogenesis and metastasis, and direct support of both neoplastic growth and inflammatory reaction. Indeed, the cells are increased in numerous pathologic conditions, including infections, inflammatory diseases, graft-versus-host disease, traumatic stress, and neoplastic diseases (Dolcetti et al., Cancer Lett. 2008 Aug. 28; 267(2):216-25; Talmadge, Clin Cancer Res. 2007 Sep. 15; 13(18 Pt 1):5243-8).

SUMMARY

This invention is based on, at least in part, an unexpected discovery that a population of stem cells prepared from an adult or young animal, blastomere-like stem cells (BLSCs), can significantly reduce the number of MDSCs in an animal.

Accordingly, one aspect of this invention features a method for treating a cellular proliferative disorder in a subject. The method includes administering to a subject in need thereof an effective amount of BLSCs.

A cellular proliferative disorder refers to a disorder characterized by uncontrolled, autonomous cell growth (including malignant and non-malignant growth), and MDSCs-mediated immunosuppression. Examples of this disorder include colon cancer, breast cancer, prostate cancer, hepatocellular carcinoma, melanoma, lung cancer, glioblastoma, brain tumor, hematopoeitic malignancies, retinoblastoma, renal cell carcinoma, head and neck cancer, cervical cancer, pancreatic cancer, esophageal cancer, ovarian cancer, and squama cell carcinoma.

A subject refers to a human or a non-human animal. Examples of a non-human animal include all vertebrates having immune systems, e.g., mammals, such as non-human primates (particularly higher primates), dogs, rodents (e.g., mice or rats), guinea pigs, cats, farm animals (e.g., horses, cows, sheep, or pigs), and non-mammals, such as birds, amphibians, reptiles, etc. In a preferred embodiment, the subject is a human. In another embodiment, the subject is an experimental animal or animal suitable as a disease model.

A subject to be treated for a cellular proliferative disorder can be identified by standard diagnosing techniques for the disorder. "Treating" refers to administration of a composition (e.g., a cell composition) to a subject, who is suffering from or is at risk for developing cellular proliferative disorder, with the purpose to cure, alleviate, relieve, remedy, delay the onset of, prevent, or ameliorate the disorder, the symptom of the disorder, the disease state secondary to the disorder, or the predisposition toward the damage/disorder. An "effective amount" refers to an amount of the composition that is capable of producing a medically desirable result in a treated subject. The treatment method can be performed alone or in conjunction with other drugs or therapies.

The invention also features a method for decreasing the level of MDSCs in a subject by administering to a subject in need thereof an effective amount of BLSCs.

In another aspect of the invention features a method for overcoming an immunosuppression in a subject. The method includes administering to a subject in need thereof an effective amount of BLSCs. The immunosuppression can be an MDSCs-mediated immunosuppression. In yet another aspect, the invention features a method for modulating immune response in a subject. The method includes administering to a subject in need thereof an effective amount of BLSCs.

In each of the above-described methods, the subject can be one having a cellular proliferative disorder, an infection, or an immunodeficiency disease. In each of the methods, the BLSCs are administered to a subject at $1 \times 10^8$ to $1 \times 10^{11}$/time, preferably at $5 \times 10^8$ to $5 \times 10^{10}$/time, or more preferably at $1 \times 10^9$ to $1 \times 10^{10}$/time. To minimize or avoid host rejections, the cells are preferably autologous to the subject. The BLSCs can be administered once every two weeks for 2 to 5 times, or more preferably, once every two weeks for 3 times. Optionally, the subject can be examined for the level of MDSCs before administering the BLSCs. If the level is statistically higher in a sample from the subject than that in a sample from a normal subject, the subject is a candidate for treatment with the above-described methods. The subject can also be examined for the level of MDSCs after administering the BLSCs to confirm the effect of the BLSCs administration. For example, if the MDSCs level after the administration is statistically lower than that prior to the administration, the BLSCs administration is effective.

The details of one or more embodiments of the invention are set forth in the description below. Other features, objects, and advantages of the invention will be apparent from the description and the claims.

DETAILED DESCRIPTION

This invention relates to using BLSCs for modulating immune response and treating related disorders such as cellular proliferative disorders and other immuno-deficiency disorders.

BLSCs are a population of non-embryonic stem cells in adult or young animals. These cells are totipotent and have the differentiation capability similar to that of embryonic stem cells. See WO2007/100845. Containing a normal chromosomal complement, BLSCs are lineage-uncommitted and can form all somatic (non-reproductive) cells of the body. They can differentiate into various lineages including those derived from ectoderm (e.g., neurons, astrocytes, oligodendrocytes, and keratinocytes), mesoderm (e.g., skeletal muscle, smooth muscle, cardiac muscle, fat tissues, cartilage, bone, dermis, blood cells, ligament tissues, tendons, and endothelial cells), and endoderm (e.g., GI epithelium, hepatocytes, oval cells, billary cells, pancreatic cells (such as α cells, β cells, and γ cells), and ductal cells). In addition, they can differentiate into spermatogonia and form the reproductive gametes sperm and/or ovum, and cells and tissues of the embryonic and fetal portions of the placenta. The cells are responsive to lineage-induction agents, proliferation agents, and differentiation inhibitory agents. On the other hand, they are unresponsive to progression agents. Similar to epiblast-like stem cells, BLSCs are not contact inhibited at confluence, but rather form multiple confluent layers of cells as long as they are maintained with an adequate nutrient supply. BLSCs do not express phenotypic expression markers for progenitor or differentiated cells, germ layer lineage stem cells, or epiblast-like stem cells. Instead, they express general and specific embryonic lineage markers, such as the embryonic stem cell markers CD66e, HCEA, CEA, and CEA-CAM-1. BLSCs are normally quiescent in adult tissues. However, when such tissues are injured, BLSCs are activated and differentiate to repair the damaged tissues.

To prepare BLSCs, one can use the methods described Example 1 below or in WO2007/100845. Generally, the cells can be isolated from many tissues of adult or young animals, including blood, bone marrow, and skeletal muscle. To confirm the cells isolated are indeed BLSCs, one can examine a number of characteristics, including (1) sizes of cells in suspension, which are less than 1 μm, (2) cell surface markers, e.g., $CD66e^+$, and (3) trypan blue staining positive. Antibodies against cell surface markers, such as CD66e can be used for identifying BLSCs. For that purpose, suitable antibodies can be conjugated with suitable labels, such as fluorescein isothiocyanate (FITC), phycoerythrin (PE), allophycocyanin (APC), or quantum dots. BLSCs can be further enriched by flow cytometry using such antibodies.

The enriched cells are then tested by standard techniques. To confirm the differentiation potential of the cells, they can be induced to form, for example, neuro-glial cells, osteocyte, and adipocyte by methods known in the art. For example, the cells can be passed and cultured to confluence, shifted to an osteogenic medium or an adipogenic medium, and incubated for suitable time (e.g., 3 weeks). See, e.g., U.S. Pat. Nos. 7,470,537, 7,374,937, and 6,777,231. The differentiation potential for osteogenesis is assessed by the mineralization of calcium accumulation, which can be visualized by von Kossa staining. To examine adipogenic differentiation, intracellular lipid droplets can be stained by Oil Red O and observed under a microscope. For neural differentiation, the cells can be incubated in a neurogenic medium for suitable duration (e.g., 7 days), and then subjected to serum depletion and incubation of β-mercaptoethanol. See, e.g., U.S. Pat. No. 7,470,537 and US Applications 20080274087, 20080213228, and 20080152629. After differentiation, cells exhibit the morphology of refractile cell body with extended neuritelike structures arranged into a network. Immunocytochemical stain of lineage specific markers can be further conducted to confirm neural differentiation. Examples of the markers include neuron specific class III β-tubulin (Tuj-1), neurofilament, and GFAP.

Alternatively, to confirm the identity of the isolated cells, one can take advantage of BLSCs' lack of contact inhibition. To that end, one can culture the isolated cells to confluence. Under that condition, BLSCs can form sphere-like cell aggregation, multiple confluent layers, or mesh-net structures. In contrast, $CD42^+$ cells or platelets cannot form the just-mentioned structure, such as cell aggregation.

The BLSCs thus confirmed can be further propagated in a non-differentiating medium culture for more than 10, 20, 50, 100, or 300 population doublings without indications of spontaneous differentiation, senescence, morphological changes, increased growth rate, or changes in ability to differentiate into neurons. The cells can be stored by standard methods before use. As described herein, BLSCs can be used to decrease the level of MDSCs in a subject.

The term "MDSCs" refers to a myeloid-derived, heterogeneous cell population encompassing contiguous stages of myelo-monocytic differentiation. This heterogeneity is reflected by a complex expression pattern of surface markers. The main phenotype of murine MDSCs is defined by the following markers: $CD11b^+$, $Gr-1^+\mu F4/80^{int}$, $CD11c^{low}$, $MHCII^{-/low}$, $Ly-6C^+$, $ER-MP58^+$, $CD31^+$ and, $IL-4R\alpha^+$. Human MDSCs have an immature phenotype, including lineage negative ($Lin^-$), $CD14^-$, human leukocyte antigen DR-negative ($HLA-DR^-$), $CD15^+$, $CD34^+$, $CD11b^-$, $CD33^+$, and $CD13^+$ (Dolcetti et al., Cancer Lett. 2008 Aug. 28; 267(2): 216-25; Talmadge, Clin Cancer Res. 2007 Sep. 15; 13(18 Pt 1):5243-8).

Tumor-bearing animals and cancer patients exhibit defects in myelopoiesis, resulting in the accumulation of MDSCs. MDSCs, recruited during neoplastic growth, are among the main inflammatory subsets that support tumor progression, acting both locally and at a systemic level. These cells can sustain tumor progression providing a favorable microenvironment in which transformed cells can proliferate, acquire new mutations, expand and evade host immuno-surveillance; moreover, MDSCs can take part in neoangiogenesis.

Thus, BLSCs-mediated repression of MDSCs can be used to treat cancer and other cellular proliferative disorders. In particular, it can be used to treat disorders that are characterized by abnormally high MSDC level. The term "cancer" refers to class of diseases that are characterized by uncontrolled cell growth, invasion, and sometimes metastasis. Cancer cells have the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type, or stage of invasiveness. Examples of cancer include, but are not limited to, carcinoma and sarcoma such as leukemia, sarcoma, osteosarcoma, lymphomas, melanoma, glioma, pheochromocytoma, hepatoma, ovarian cancer, skin cancer, testicular cancer, gastric cancer, pancreatic cancer, renal cancer, breast cancer, prostate cancer, colorectal cancer, cancer of head and neck, brain cancer, esophageal cancer, bladder cancer, adrenal cortical cancer, lung cancer, bronchus cancer, endometrial cancer, nasopharyngeal cancer, cervical or liver cancer, and cancer of unknown primary site.

MDSCs have been described in pathologies other than tumors, which involve inflammatory immune reactions such as super-antigen stimulation, and infections such as trypanosomiasis, salmonellosis, and candidiasis. For example, increased numbers of MDSCs are found to be associated with inflammatory, infectious, and graft-versus-host diseases where they restrain exuberant or novel T-cell responses (Talmadge, Clin Cancer Res. 2007 Sep. 15; 13(18 Pt 1):5243-8). MDSCs have shown to induce a profound state of immune suppression by reducing activated T-cell number and inhibit their function by multiple mechanisms, including depletion of L-arginine by arginase-1 (ARG 1) production of nitric oxide, reactive oxygen species, and reactive nitrogen oxide species by inducible nitric oxide synthase. Thus, BLSCs-mediated repression of MDSCs may also be used in developing strategies that allow the elimination of MDSCs not only for oncology but also for graft-versus-host disease, inflammation, and autoimmune diseases.

Within the scope of this invention is a method of treating an MDSCs-mediated immuno-deficiency disorder, alleviating the symptom of the disorder, or delaying the onset of the disorder in a subject. One example of the disorder is a cellular proliferative disorder. A subject to be treated can be identified by standard techniques for diagnosing the conditions or disorders of interest. In particular, the subject can be identified if the level of MDSCs in the subject is significantly higher than a previous MDSC level of the same subject, or is higher than that of a normal subject. The treatment method entails administering to a subject in need thereof an effective amount of the above-described BLSCs.

Accordingly, the present invention provides for BLSCs in pharmaceutical compositions. Pharmaceutical compositions can be prepared by mixing a therapeutically effective amount of BLSCs and, optionally other active substance, with a pharmaceutically acceptable carrier. The carrier can have different forms, depending on the route of administration. Examples of other active substance include compounds that inhibit the immunosuppression activity of MDSCs, interfere with the recruitment of MDSCs, or improve body's immune functions.

The above-described pharmaceutical compositions can be prepared by using conventional pharmaceutical excipients and methods of preparation. All excipients may be mixed with disintegrating agents, solvents, granulating agents, moisturizers, and binders. As used herein, the term "effective amount" or 'therapeutically effective amount' refers to an amount which results in measurable amelioration of at least one symptom or parameter of a specific disorder. A therapeutically effective amount of the BLSCs can be determined by methods known in the art. An effective amount for treating a disorder can easily be determined by empirical methods known to those of ordinary skill in the art. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of the above-described disorders is within the scope of the invention. Clinically significant attenuation or amelioration means perceptible to the patient and/or to the physician.

The phrase "pharmaceutically acceptable" refers to molecular entities and other ingredients of such compositions that are physiologically tolerable and do not typically produce unwanted reactions when administered to a human. Preferably, the term "pharmaceutically acceptable" means approved by a regulatory agency of the federal or a state government or listed in the U.S. Pharmacopeia or other generally recognized pharmacopeia for use in mammals, and more particularly in humans. Pharmaceutically acceptable salts, esters, amides, and prodrugs refers to those salts (e.g., carboxylate salts, amino acid addition salts), esters, amides, and prodrugs which are, within the scope of sound medical judgment, suitable for use in contact with the tissues of patients without undue toxicity, irritation, allergic response, and the like, commensurate with a reasonable benefit/risk ratio, and effective for their intended use.

A carrier applied to the pharmaceutical compositions described above includes a diluent, excipient, or vehicle with which a compound is administered. Such pharmaceutical carriers can be sterile liquids, such as water and oils. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The BLSCs can be administered to individuals through infusion or injection (for example, intravenous, intrathecal, intramuscular, intraluminal, intratracheal, intraperitoneal, or subcutaneous), orally, transdermally, or other methods known in the art. In one example, the cells can be directly injected at a site or into a tissue (e.g., liver or pancreas), where a tumor or immunosuppression is found Administration may be once every two weeks, once a week, or more often, but frequency may be decreased during a maintenance phase of the disease or disorder.

Both heterologous and autologous BLSCs can be used. In the former case, HLA-matching should be conducted to avoid or minimize host reactions. In the latter case, autologous BLSCs are enriched and purified from a subject and stored for later use. Host BLSCs may be cultured in the presence of host or graft T cells ex vivo and re-introduced into the host. This may have the advantage of the host recognizing the BLSCs as self and better providing reduction in T cell activity.

The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the above-described composition. Dosages and administration regimen can be adjusted depending on the age, sex, physical condition of administered as well as the benefit of the conjugate and side effects in the patient or mammalian subject to be treated and the judgment of the physician, as is appreciated by those skilled in the art.

It has been reported that MDSCs recruitment to a tumor site could be triggered by a variety of tumor-derived soluble factors, which profoundly affect myelopoiesis and obilization of myeloid cells as well as their activation (Dolcetti et al., Cancer Lett. 2008 Aug. 28; 267(2):216-25). Totipoent or pluripotent stem cells (such as BLSCs) may intervene in MDSCs' activation or migration, or promote differentiation of MDSCs, thereby overcoming MDSCs-mediated immunosuppression.

Accordingly, totipoent or pluripotent stem cells other than BLSCs can also be used for treating the above-mentioned immunodeficiency disorders that are characterized by MDSCs accumulation. Examples of such totipoent or pluripotent stem cells include cells derived from the above-described BLSCs, such as SBR cells and SBT cells that are derived by incubating the BLSCs with retinoid acid and TGF-β, respectively. Examples the totipoent or pluripotent stem cells may also include embryonic stem cells (ES cells), adherent BLSCs (aBLSCs), transitional BLSCs (trBLSCs), and epiblast-like stem cells (ELSCs) as described in WO2007/100845. Thus, within the scope of this invention are methods of using these totipoent or pluripotent stem cells to treat above-mentioned immunodeficiency disorders.

Treatment strategies based on stem cells from adult or young animals, such as BLSCs, enjoy a number of advantages over that based on ES cells. First, given the good markers, BLSCs are easy to obtain from tissues from adult or young animals. Second, a large number of BLSCs can be obtained from blood (more than $2\times10^8$/ml). Third, BLSCs are easy to maintain and expand and to be induced to differentiate into lineage specific cells. Forth, BLSCs, once introduced into a subject, do not develop into a teratoma and therefore are safer than ES cells. Last but not least, obtaining and using BLSCs do not involve manipulating or killing embryos and associated ethical issues.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

EXAMPLE 1

Isolation of BLSCs

Methods for activation, purification, and expansion of BLSCs have been described in WO/2007/100845. In this example, BLSCs were purified from the blood of human subjects using two methods, a plasma fraction method and a hemolysis method.

Briefly, for the plasma fraction method, a whole blood sample (1 ml) was prepared from a first human subject using a standard method. The sample was then stored at 4° C. for about 7-9 days and BLSCs were enriched from the sample in the manner described in WO/2007/100845.

The hemolysis method was used to obtain a hemolysis fraction in the manner described in WO/2007/100845. Briefly, about 1 ml of whole blood is obtained from a second human subject and stored at about 4° C. in the presence of EDTA or other $Ca^{2+}$ complexing agents for about 9 days in a transport medium (e.g., Moraga medium with catalog number MBC-HUB-MED-100-A004, Moraga Biotechnology Corporation, Los Angeles, Calif.). After 9 days, the red cells in the whole blood sample were lysed using about 50 ml of a sterile hemolysis solution (e.g., MBC-ASB-REBG-900A-001). After centrifugation (e.g., at 1800×g, 10 minutes) to remove debris and lysed cells, the cell pellet was re-suspended in 2 ml of a Moraga sterile reconstitution solution (MBC-ASB-REBG-900A-002).

The above-described two cell populations were analyzed by flow cytometry using FITC-labeled anti-CD 10 antibody, PE-labeled anti-CD66e antibody, APC-labeled anti-CD90 antibody. The results are summarized in Table 1 below.

TABLE 1

| | Percentage of Isolated Cells (%) | |
| --- | --- | --- |
| Markers | Hemolysis method | Plasma fraction method |
| $CD10^-CD66e^+$ | 5.81 | 9.14 |
| $CD10^+CD66e^+$ | 66.67 | 2.99 |
| $CD10^+CD66e^-$ | 3.11 | 1.10 |
| $CD10^-CD90^+$ | 0.62 | 9.80 |
| $CD10^+CD90^+$ | 13.65 | 2.20 |
| $CD10^+CD90^-$ | 55.13 | 1.46 |

As shown in Table 1, when using the hemolysis method, about 5.81%, 66.67%, and 3.11% of the isolated cells were BLSCs ($CD10^-CD66e^+$), transitional BLSCs (trBLSCs, $CD10^+CD66e^+$), and epiblast-like stem cells (ELSCs, $CD10^+CD66e^-$), respectively. About 0.62%, 13.65%, and 55.13% of the cells were $CD10^-CD90^+$, $CD10^+CD90^+$ (transitional epiblast-like stem cells, trELSCs), and $CD10^+CD90^-$, respectively. BLSCs were further enriched based on their markers ($CD10^-CD66e^+$). This method yielded about $200\times10^6$ BLSCs/ml blood.

When using the plasma faction methods, about 9.14%, 2.99%, and 1.10% of the isolated cells were BLSCs, transitional BLSCs, and ELSCs, respectively. About 9.8%, 2.2%, and 1.46% of the cells were $CD10^-CD90^+$, $CD10^+CD90^+$ (trELSCs), $CD10^+CD90^-$, respectively. This method yielded about $239\times10^6$ BLSCs/ml plasma.

The BLSCs were trypan blue staining positive and generally smaller than 1 μm in size, which was different from that of platelets ($CD42^+$ and trypan blue staining negative). Especially, unlike platelets, which lack nuclei, do not proliferate and differentiate, the BLSCs could proliferate in a medium and be maintained and expanded in an undifferentiated status in the manner described in WO/2007/100845. The BLSCs lacked contact inhibition and could form sphere-like cell aggregation, multiple confluent layers, and mesh-net structures. Aggregation of the cells led to change the cell morphology. In contrast, $CD42^+$ cells or platelets did not form the just-mentioned structures, such as cell aggregation.

The BLSCs were then tested for their differentiation capacity in the manner described in WO/2007/100845 or other methods known in the art. It was found that, upon induction under conditions known in the art, the cells differentiated into various lineages including those derived from ectoderm, mesoderm, endoderm, and spermatogonia. They could be maintained and expanded in the undifferentiated status for over 300 passages without losing the differentiation potentials. They did not form teratoma.

EXAMPLE 2

In Vivo Activity of BLSCs

BLSCs were purified from a human subject according to the methods described above and administered autologously to the same subject at $1\times10^9$ cells. At Days 0, 14, and 28 after administration, blood samples were obtained from the person. Cytometry analysis was then conducted to examine the blood levels of MDSCs and Treg. It was found that, at Days 0, 14, and 28, MDSCs ($CD14^-CD33^+CD11b^+Lin^-$) levels were 9.24%, 2.19%, and 0.35% of total peripheral blood mononuclear cells (PBMC), respectively. These results indicate BLSCs significantly decreased the level of MDSCs in a subject and therefore can be used to treat patients having a MDSCs-related immunodeficiency disorder.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for overcoming immunosuppression in a human subject, the method comprising
    administering intravenously to a human subject in need thereof an effective amount of human blastomere-like stem cells, and
    overcoming immunosuppression in the subject,
wherein the immunosuppression is myeloid-derived suppressor cells-mediated immunosuppression, the blastomere-like stem cells being isolated from human blood and autologous to the subject.

2. The method of claim 1, wherein the blastomere-like stem cells are administered at $1\times10^8$ to $1\times10^{11}$ cells each time.

3. The method of claim 2, wherein the blastomere-like stem cells are administered at $5\times10^8$ to $5\times10^{10}$ cells each time.

4. The method of claim 3, wherein the blastomere-like stem cells are administered at $1\times10^9$ to $1\times10^{10}$ cells each time.

5. The method of claim 1, wherein the blastomere-like stem cells are administered once every two weeks for 2 to 5 times.

6. The method of claim 5, wherein the blastomere-like stem cells are administered once every two weeks for three times.

7. The method of claim 1, wherein the method further comprises determining the level of myeloid-derived suppressor cells in the subject before or after administering the blastomere-like stem cells.

8. The method of claim 7, wherein the level of myeloid-derived suppressor cells is decreased after the administering step as compared to before the administering step.

9. The method of claim 1, wherein the blastomere-like stem cells are less than 1 μm in size, trypan blue staining positive, and $CD66e^+$.

* * * * *